(12) United States Patent  (10) Patent No.: US 7,702,527 B1
Kron et al.  (45) Date of Patent: Apr. 20, 2010

(54) TECHNIQUES FOR ILLUSTRATING AND ANALYZING LONG TERM HEALTH CARE EXPENSES

(75) Inventors: Robert Kron, Franklin Park, NJ (US); Walter Veghte, Cranbury, NJ (US); Roseanne Bassin, West Windsor, NJ (US); Eileen Russo, Cranbury, NJ (US); Steve Monical, Monmouth Junction, NJ (US)

(73) Assignee: Merrill Lynch Co., Inc., New York, NY (US)

( * ) Notice: Subject to any disclaimer, the term of this patent is extended or adjusted under 35 U.S.C. 154(b) by 3094 days.

(21) Appl. No.: 09/850,783

(22) Filed: May 8, 2001

(51) Int. Cl.
*G06Q 40/00* (2006.01)
(52) U.S. Cl. .................. 705/4; 705/2; 705/3; 705/36
(58) Field of Classification Search .......... 705/2–4, 705/36
See application file for complete search history.

(56) References Cited

U.S. PATENT DOCUMENTS

| | | | |
|---|---|---|---|
| 5,136,502 A * | 8/1992 | Van Remortel et al. ........ 705/2 |
| 5,191,522 A | 3/1993 | Bosco et al. |
| 5,519,607 A | 5/1996 | Tawil |
| 5,590,037 A | 12/1996 | Ryan et al. |
| 5,704,044 A | 12/1997 | Tarter et al. |
| 5,802,500 A | 9/1998 | Ryan et al. |
| 5,826,243 A | 10/1998 | Musmanno et al. |
| 5,866,889 A | 2/1999 | Weiss et al. |
| 5,991,744 A | 11/1999 | DiCresce |
| 5,995,937 A | 11/1999 | DeBusk et al. |
| 6,009,402 A | 12/1999 | Whitworth |
| 6,012,035 A | 1/2000 | Freeman, Jr. et al. |
| 6,012,043 A | 1/2000 | Albright et al. |
| 6,014,632 A | 1/2000 | Gamble et al. |
| 6,026,364 A | 2/2000 | Whitworth |
| 6,029,156 A | 2/2000 | Lannert et al. |
| 6,032,141 A | 2/2000 | O'Connor et al. |
| 6,044,351 A | 3/2000 | Jones |
| 6,061,657 A | 5/2000 | Whiting-O'Keefe |
| 6,064,998 A | 5/2000 | Zabloudil et al. |

(Continued)

OTHER PUBLICATIONS

Questioning the Adequacy of Long-Term Care IRAs, by Smallwood et al., Health Affairs, Summer 1987; vol. 6, Iss.2, p. 132, pp. 1-2.*

*Primary Examiner*—Vanel Frenel
(74) *Attorney, Agent, or Firm*—Baker Botts L.L.P.

(57) ABSTRACT

A computer-executable method for financial retirement planning that provides a comparative evaluation of a plurality of health care funding alternatives. The comparative evaluation enables individuals to select one or more funding alternatives appropriate to their particular set of circumstances. The method commences by calculating overall cash flow for an individual, a couple, and/or a family during retirement. Based upon this cash flow, an amount representing an affordable heath care insurance premium is determined. Next, a comparison of projected retirement finances is provided. This comparison provides (a) financial projections assuming that long-term health care will not be required, (b) financial projections if long-term health care is required, but the individual is not covered by insurance, and (c) financial projections if long-term health care is required, and the individual is covered by insurance. The financial projections include a level of attainable retirement spending per week, month, and/or year. Optionally, the projections include a low-cost estimate, an average cost estimate, and a high-cost estimate for the expenses of long-term health care and/or health care insurance.

12 Claims, 16 Drawing Sheets

U.S. PATENT DOCUMENTS

| | | |
|---|---|---|
| 6,067,537 A | 5/2000 | O'Connor et al. |
| 6,067,538 A | 5/2000 | Zorba et al. |
| 6,073,127 A | 6/2000 | Lannert et al. |
| 6,076,072 A | 6/2000 | Libman |
| 6,108,641 A | 8/2000 | Kenna et al. |
| 6,163,770 A | 12/2000 | Gamble et al. |
| 6,177,940 B1 | 1/2001 | Bond et al. |
| 6,205,434 B1 | 3/2001 | Ryan et al. |
| 6,208,973 B1 | 3/2001 | Boyer et al. |

* cited by examiner

ESTIMATED ANNUAL COST: LONG-TERM HEALTH CARE INSURANCE POLICY

|  | LOW COST | AVERAGE COST | HIGH COST |
|---|---|---|---|
| CLIENT: | $1,600 | $2,350 | $4,400 |
| CLIENT'S SPOUSE: | $1,500 | $2,250 | $4,200 |

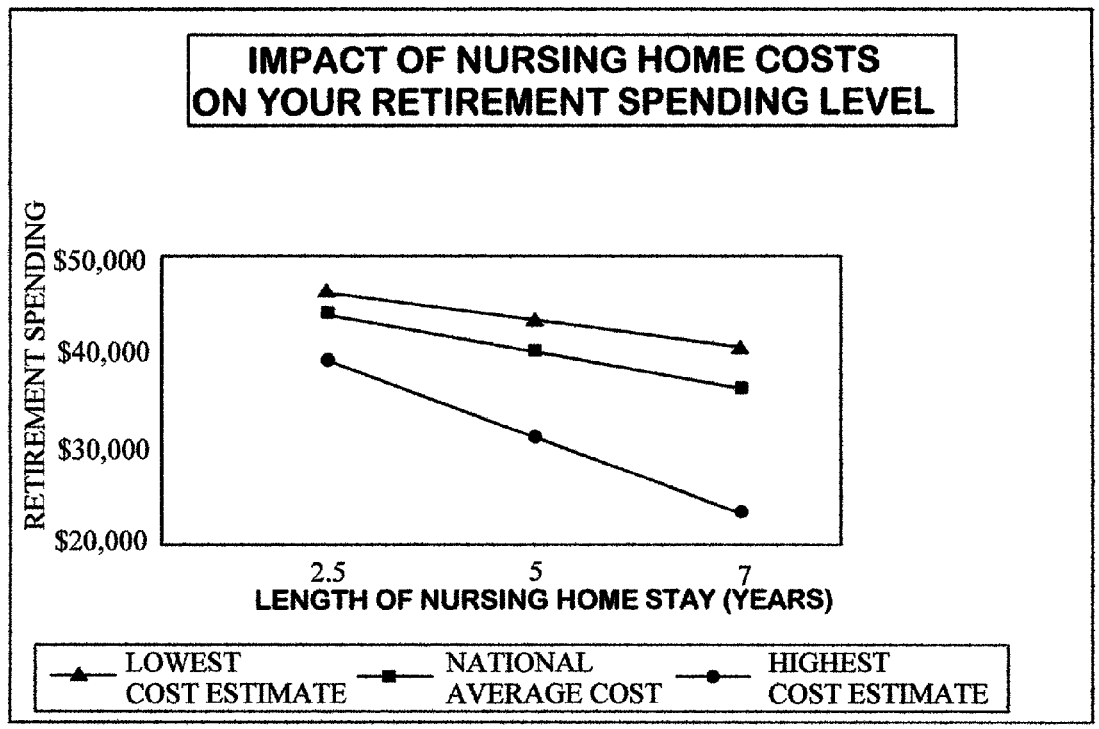

FIG. 9

| | ANNUAL RETIREMENT SPENDING LEVEL | | | |
|---|---|---|---|---|
| | LONG-TERM CARE INSURANCE | NURSING HOME COSTS FUNDED OUT OF POCKET | | |
| | ANY LENGTH STAY* | 2.5 YEARS | 5 YEARS | 7 YEARS |
| LOW COST ESTIMATE | $49,000 | $46,500 | $43,500 | $40,000 |
| AVG. COST ESTIMATE | $48,000 | $44,000 | $39,000 | $34,500 |
| HIGH COST ESTIMATE | $45,000 | $39,000 | $31,000 | $23,000 |

*NOTE: LONG-TERM CARE INSURANCE POLICIES ARE TYPICALLY AVAILABLE WITH TWO-YEAR, THREE-YEAR, FOUR-YEAR, OR LIFE COVERAGE. FOR YOUR ANALYSIS, LIFE COVERAGE WAS ASSUMED.

FIG. 10

| LONG-TERM CARE INSURANCE COST COMPARISON BY AGE ||
|---|---|
| AGE AT PURCHASE | YEARLY PREMIUM* |
| 60 | $1,719 |
| 65 | $2,580 |
| 70 | $3,723 |
| 75 | $6,734 |

FIG. 11

STANDARD MEDIGAP FEATURES

| POLICY TYPE | A | B | C | D | E | F | G | H | I | J |
|---|---|---|---|---|---|---|---|---|---|---|
| BASIC BENEFITS | ✓ | ✓ | ✓ | ✓ | ✓ | ✓ | ✓ | ✓ | ✓ | ✓ |
| PART A-HOSPITAL DEDUCTIBLE | | ✓ | ✓ | ✓ | ✓ | ✓ | ✓ | ✓ | ✓ | ✓ |
| PART B- DOCTOR DEDUCTIBLE | | | ✓ | | | ✓ | | | | ✓ |
| 20% CO-INSURANCE | ✓ | ✓ | ✓ | ✓ | ✓ | ✓ | ✓ | ✓ | ✓ | ✓ |
| PART B-% EXCESS DOCTOR BILL | | | | | | 100% | 80% | | 100% | 100% |
| ADDITIONAL 365 HOSPITAL DAYS | ✓ | ✓ | ✓ | ✓ | ✓ | ✓ | ✓ | ✓ | ✓ | ✓ |
| SKILLED-NURSING CO-INSURANCE | | | ✓ | ✓ | ✓ | ✓ | ✓ | ✓ | ✓ | ✓ |
| AT-HOME CARE | | | | ✓ | | | ✓ | ✓ | ✓ | ✓ |
| PRESCRIPTION CARE | | | | | | | | ✓ | ✓ | ✓ |
| PREVENTIVE CARE | | | | | ✓ | | | | | ✓ |
| HEALTH CARE ABROAD | | | ✓ | ✓ | ✓ | ✓ | ✓ | ✓ | ✓ | ✓ |

FIG. 12

ONE CLIENT

| LONG-TERM CARE INSURANCE COMPARISION* | | |
|---|---|---|
| TIME OF PURCHASE | ESTIMATED ANNUAL PREMIUM | TOTAL COST (IN TODAY'S DOLLARS)** |
| TODAY | $1,486 | $61,688 |
| 5 YEARS FROM NOW | $1,673 | $64,066 |
| 10 YEARS FROM NOW | $2,188 | $73,136 |
| 15 YEARS FROM NOW | $2,948 | $84,322 |
| 20 YEARS FROM NOW | $4,294 | $97,068 |
| * ASSUMES $130 PER DAY BENEFIT, ADJUSTED FOR INFLATION, AND LIFETIME COVERAGE. ** REPRESENTS THE TOTAL COST OF ALL PAYMENTS IN TODAY'S DOLLARS ASSUMING THAT YOU PURCHASE LONG-TERM CARE INSURANCE AT SPECIFIED TIME AND CONTINUE PAYMENTS THROUGH THE END OF YOUR RETIREMENT ANALYSIS. | | |

FIG. 13

TWO CLIENTS

| LONG-TERM CARE INSURANCE COMPARISION* | | | | |
|---|---|---|---|---|
| TIME OF PURCHASE | ESTIMATED ANNUAL PREMIUM | | COMBINED TOTAL | TOTAL COST (IN TODAY'S DOLLARS)** |
| | JIM | JANE | | |
| TODAY | $1,486 | $1,427 | $2,913 | $76,755 |
| 5 YEARS FROM NOW | $1,673 | $1,638 | $3,311 | $99,330 |
| 10 YEARS FROM NOW | $2,188 | $2,059 | $4,247 | $106,175 |
| 15 YEARS FROM NOW | $2,948 | $2,773 | $5,721 | $114,420 |
| 20 YEARS FROM NOW | $4,294 | $3,896 | $8,190 | $122,850 |
| * ASSUMES $130 PER DAY BENEFIT, ADJUSTED FOR INFLATION, AND LIFETIME COVERAGE. ** REPRESENTS THE TOTAL COST OF ALL PAYMENTS IN TODAY'S DOLLARS ASSUMING THAT YOU PURCHASE LONG-TERM CARE INSURANCE AT SPECIFIED TIME AND CONTINUE PAYMENTS THROUGH THE END OF YOUR RETIREMENT ANALYSIS. | | | | |

FIG. 14

| SUMMARY OF LTCI POLICY COMPONENTS ||| 
|---|---|---|
| POLICY FEATURE | EXPLANATION | POINTS OF COMPARISION AND COST CONSIDERATION |
| BENEFIT AMOUNT | ❖ GENERALLY QUOTED AS A PERDIEM AMOUNT THAT YOU WILL RECEIVE FROM YOUR POLICY ON A DAILY, ANNUAL, WEEKLY OR OTHER BASIS.<br>• THE HOME CARE BENEFIT CAN BE ANYWHERE FROM 50-100% OF THE AMOUNT PAID FOR NURSING HOME CARE. | ❖ COMPARE THE PREMIUM COSTS FOR DIFFERENT BENEFIT AMOUNTS AGAINST LONG-TERM CARE COSTS IN YOUR AREA.<br>• HIGHER BENEFIT AMOUNTS WILL REQUIRE HIGHER PREMIUMS. |
| ELIMINATION PERIOD | ❖ THE AMOUNT OF TIME BETWEEN WHEN YOU REQUIRE LONG-TERM CARE SERVICES AND WHEN YOU RECEIVE POLICY BENEFITS.<br>• YOU CAN CHOOSE IMMEDIATE COVERAGE, OR A WAITING PERIOD OF UP TO 100 DAYS. | ❖ COMPARE THE INCREASE IN PREMIUM WITH THE DELAY IN AVAILABILITY OF BENEFITS.<br>• SHORTER ELIMINATION PERIODS RESULT IN HIGHER POLICY PREMIUMS. |
| THE BENEFIT PERIOD | ❖ THE LENGTH OF TIME THAT YOU WILL RECEIVE BENEFITS FROM YOUR POLICY. | ❖ COMPARE THE BENEFIT PERIOD WITH THE PREMIUM COST.<br>• LONGER BENEFIT PERIODS HAVE HIGHER PREMIUM COSTS. |
| LIFETIME MAXIMUM BENEFITS | ❖ THE TOTAL MAXIMUM BENEFIT THAT WILL BE PAID OUT OVER THE DURATION OF THE POLICY. | ❖ COMPARE THE PREMIUM COST OF LIFETIME BENEFITS WITH YOUR ALTERNATIVE MEANS AVAILABLE TO PAY FOR CARE IF THE POLICY BENEFITS RUN OUT. |
| INFLATION PROTECTION RIDER | ❖ PROVIDES THE ABILITY TO INCREASE YOUR BENEFIT AMOUNT BASED ON INFLATION, USUALLY LIMITED TO 5% PER YEAR COMPOUNDED. | ❖ COMPARE THE POTENTIAL PREMIUM INCREASES WITH THE INCREASED COVERAGE AVAILABLE. |

FIG. 15

(CONTINUED FROM FIG. 15)

| SUMMARY OF LTCI POLICY COMPONENTS | | |
|---|---|---|
| POLICY FEATURE | EXPLANATION | POINTS OF COMPARISION AND COST CONSIDERATION |
| BENEFIT ELIGIBILITY | ❖ ALL POLICIES CONTAIN PROVISIONS THAT DETERMINE WHEN BENEFITS ARE PAYABLE. | ❖ QUALIFIED POLICIES MUST BE TRIGGERED BY:<br>• COGNITIVE IMPARIMENT (SUCH AS ALZHEIMER'S DISEASE)<br>• NEED FOR ASSISTANCE WITH AT LEAST TWO ACTIVITIES OF DAILY LIVING (ADLS).<br>❖ INSURERS CAN SET THEIR OWN STANDARDS FOR NON-QUALIFIED POLICIES. |
| BENEFIT PAYMENT METHODS | ❖ BENEFITS CAN BE PAID BASED ON:<br>• EXPENSE INCURRED METHOD<br>INDEMNITY METHOD | ❖ THE "EXPENSE INCURRED METHOD" PAYS BASED ON CLAIMS THAT YOU SUBMIT.<br>❖ THE "INDEMNITY METHOD" PAYS SPECIFIED BENEFITS TO YOU REGARDLESS OF THE SERVICES RENDERED. |

FIG. 16

| SUMMARY OF LTCI POLICY COMPONENTS ||||||
|---|---|---|---|---|
| HEALTH CARE SOURCE | WHAT IS COVERED | WHAT IS NOT COVERED | ELIGIBILITY | COST OF BENEFITS |
| MEDICAID | ❖ CUSTODIAL AND MEDICAL CARE IN A NURSING HOME.<br>❖ HOSPITAL AND DOCTOR CARE.<br>❖ SKILLED NURSING FACILITY CARE. | ❖ ACUTE CARE.<br>❖ HOSPITAL CARE. | ❖ AGE 65 OR DISABILITY.<br>❖ YOU MUST QUALIFY AS INDIGENT ACCORDING TO STATE-DEFINED POVERTY LEVEL BASED ON INCOME AND ASSETS. | ❖ LITTLE OR NO COST IF MEET REQUIREMENTS. |
| LONG-TERM CARE INSURANCE (LTCI) | ❖ CUSTODIAL AND MEDICAL CARE IN A NURSING HOME.<br>❖ HOME HEALTH CARE. | ❖ HOSPITAL AND DOCTOR CARE. | ❖ SUBJECT TO AGE RESTRICTIONS (TYPICALLY NOT AVAILABLE AFTER MID SEVENTIES.<br>❖ SOME RESTRICTIONS ON PRE-EXISTING CONDITIONS. | ❖ PAY ANNUAL PREMIUMS - RANGE BASED ON AGE AND POLICY FEATURES. |
| LIFE CARE COMMUNITY | ❖ BROAD ARRAY OF POTENTIAL BENEFITS.<br>❖ HOUSING OPTIONS.<br>❖ GENERALLY GUARANTEED SPACE IN NURSING HOME.<br>❖ COVERAGE IN SKILLED NURSING FACILITIES.<br>❖ SOME HEALTH BENEFITS. | ❖ DEPENDS ON CONTRACT ARRANGEMENTS. | ❖ SUBJECT TO AGE RESTRICTIONS (TYPICALLY NOT AVAILABLE AFTER MID SEVENTIES.<br>❖ SOME RESTRICTIONS ON PRE-EXISTING CONDITIONS. | ❖ MAJOR COST IS HOUSING RELATED.<br>❖ HEALTH CARE IS GENERALLY AN ADD ON. |

FIG. 17

| SUMMARY OF LTCI POLICY COMPONENTS ||||||
|---|---|---|---|---|
| HEALTH CARE SOURCE | WHAT IS COVERED | WHAT IS NOT COVERED | ELIGIBILITY | COST OF BENEFITS |
| EMPLOYER PROVIDED RETIREE HEALTH CARE. | ✦ HOSPITAL AND DOCTOR CARE.<br>✦ HOME HEALTH CARE.<br>✦ STRUCTURED SIMILARLY TO PRE-RETIREMENT HEALTH CARE INSURANCE. | ✦ CUSTODIAL AND MEDICAL CARE IN A NURSING HOME.<br>✦ EXPERIMENTAL PROCEDURES. OTHER LIMITATIONS SIMILAR TO PRE-RETIREE COVERAGE. | ✦ ROUGHLY 1/3 OF EMPLOYERS<br>✦ PROVIDE RETIREE HEALTH COVERAGE. | ✦ COMPARABLE TO PRE-RETIREMENT BUT GENERALLY HIGHER DEDUCTIBLES AND CO-PAYMENTS. |
| COBRA | ✦ CONTINUATION OF EMPLOYER BENEFIT PLANS FOR A SPECIFIED LENGTH OF TIME.<br>• 18 MONTHS FOR RETIREMENT OR TERMINATION OF EMPLOYMENT.<br>• 36 MONTHS FOR ALL OTHER QUALIFYING EVENTS. | ✦ SAME LIMITATIONS AS YOUR EMPLOYER PROVIDED HEALTH BENEFITS. | ✦ RETIREMENT TERMINATION OF EMPLOYMENT, DIVORCE OR SEPARATION, DEATH OR CHILD NO LONGER A DEPENDENT. | ✦ GROUP RATES APPLY BUT FULL COST PAID BY PARTICIPANT.<br>✦ TYPICALLY AN ADDITIONAL 2% ADMINISTRATIVE CHARGE. |

FIG. 18

SUMMARY OF LTCI POLICY COMPONENTS

| HEALTH CARE SOURCE | WHAT IS COVERED | WHAT IS NOT COVERED | ELIGIBILITY | COST OF BENEFITS |
|---|---|---|---|---|
| INDIVIDUAL HEALTH INSURANCE POLICIES | ❖ SIMILAR TO EMPLOYER ❖ PROVIDED INSURANCE. | ❖ SIMILAR LIMITATIONS AS TRADITIONAL POLICIES. | ❖ SOMETIMES PROHIBITIVELY EXPENSIVE. | ❖ MORE EXPENSIVE THAN GROUP INSURANCE. |
| MEDICARE | ❖ HOSPITAL & DOCTOR CARE.<br>• HOSPITAL CARE FOR 90 DAYS.<br>• 60 LIFETIME RESERVE DAYS.<br>• TRADITIONAL DOCTOR SERVICES. WITH SOME QUALIFICATIONS:<br>• AT HOME CARE.<br>• SKILLED NURSING FACILITIES CARE.<br>• HOSPICE CARE. | ❖ CUSTODIAL AND MEDICAL CARE IN A NURSING HOME.<br>❖ DENTAL CARE AND DENTURES.<br>❖ PRESCRIPTION DRUGS.<br>❖ ROUTINE CHECKUP.<br>❖ EYE GLASSES. HEARING AIDS AND PRIVATE DUTY NURSES. | ❖ SOCIAL SECURITY ELIGIBLE.<br>❖ NOT AVAILABLE UNTIL AGE 65 OR IN EVENT OF DISABILTY.<br>❖ COVERS OVER 90% OF PEOPLE AGE 65 OR OLDER. | ❖ DEDUCTIBLES.<br>❖ CO-PAYS.<br>❖ EXCLUSIONS. |
| MEDIGAP INSURANCE | ❖ 10 STANDARDIZATION POLICIES COVERING AN INCREASING NUMBER OF THE ITEMS NOT COVERED BY MEDICARE. | ❖ CUSTODIAL AND MEDICAL CARE IN A NURSING HOME. | ❖ AUTOMATIC AT AGE 65.<br>❖ CAN BE TURNED DOWN DUE TO HEALTH PROBLEMS. | ❖ VARIES DEPENDING ON POLICY CHOSEN & GEOGRAPHIC LOCATION. |

FIG. 19

| | |
|---|---|
| AMERCAN ASSOCIATION OF RETIRED PERSONS<br>601 E. ST. NW<br>WASHINGTON, D.C., 20049<br>(800)-424-3410 | www.aarp.org |
| DEPARTMENT OF LABOR | www.dol.gov |
| HEALTHCARE FINANCING ADMINISTRATION<br>7500 SECURITY BLVD.<br>BALTIMORE, MD., 21244<br>(410)-786-3000 | www.hefa.gov |
| MEDICARE<br>SEE SOCIAL SECURITY ADMINISTRATION | www.medicare.gov |
| NATIONAL ACADEMY OF ELDER LAW ATTORNEYS<br>1604 NORTH COUNTRY CLUB ROAD<br>TUCSON, AZ., 85716<br>(520)-881-4005 | www.naela.com |
| SOCIAL SECURITY ADMINISTRATION<br>OFFICE OF PUBLIC INQUIRES<br>6401 SECURITY BLVD.<br>ROOM 4-C-5 ANNEX<br>BALTIMORE, MD., 21235-6401<br>(800)-772-1213 | www.ssa.gov |

FIG. 20

| ASSETS AVAILABLE TO HEIRS | | | |
|---|---|---|---|
| | 2.5 YR. STAY | 5 YR. STAY | 7 YR. STAY |
| LONG-TERM CARE INSURANCE | $7.9 MILLION | $7.9 MILLION | $7.7 MILLION |
| OUT-OF-POCKET FUNDING | $7.7 MILLION | $7.2 MILLION | $6.7 MILLION |
| +/- ASSETS TO HEIRS | $200,000 | $700,000 | $1.2 MILLION |

FIG. 21

TECHNIQUES FOR ILLUSTRATING AND ANALYZING LONG TERM HEALTH CARE EXPENSES

FIELD OF THE INVENTION

The invention relates to machine-executable techniques for performing financial calculations related to long-term health care expenses.

BACKGROUND ART

According to the New England Journal of Medicine, there is a 43% chance that a person who lives beyond the age of 65 will require long-term health care. The U.S. Department of Commerce reports that 8.8 million people over the age of 65 are receiving long-term care at the present time. Of this 8.8 million, 1.3 million are nursing home residents and 7.5 million receive some type of at-home care. The financial implications of long-term health care are significant. Seventy percent of single people who enter a nursing home are impoverished within one year. Fifty percent of all couples are impoverished within one year after a spouse enters a nursing home.

Perhaps the greatest threat of all to retirement security is the high cost of long-term health care. These costs are staggering. For example, a skilled nursing visit in 1990 averaged about $79 per visit, resulting in an annual cost of $12,324 for three skilled nursing visits a week. The average cost of one year at a nursing home is $47,000, but this figure increases dramatically for nursing homes located in major metropolitan areas. Average one-year nursing home costs in the New York City-Long Island Metropolitan Area run close to $78,000.

Nursing home and other long-term health care costs are not covered by Medicare. Medicare will only pay for hospitalization and doctor bills with a deductible that can be covered via any of a number of Medigap insurance policies. When a catastrophic illness or infirmity strikes, and the need for some type of long-term care is inevitable, there are only three funding options: cash, Medicaid, and long-term health care insurance. There is no one "best" funding option for everyone—it really depends upon financial circumstances that are specific to the individual requiring long-term health care.

For individuals who are wealthy and well-to-do, the best option may be to pay for long-term costs with cash, on an as-needed basis. After all, not everyone requires long-term care, and, in this ideal scenario, financial resources would be applied to insurance that is never used. On the other hand, if illness does strike, there are no problems with meeting expenses out-of-pocket. However, if such individuals wish to leave a "nest egg" to one or more heirs, the purchase of a long-term health care insurance policy may prove desirable. In the event of a serious illness, the insurance policy would serve to protect such a "nest egg" from erosion. Medicaid is not a viable funding option for wealthy clients, inasmuch as financial resources must be exhausted as a condition for eligibility.

Medicaid is a federal and state-administered health insurance program for the "poor". At present, Medicaid pays for the care of two-thirds of all nursing home residents. This is not because a disproportionate number of elderly people are poor. After all, the median income of an elderly couple is $2270 a month—two and a half times the poverty level for a family of two. Rather, it is attributable to the fact that an extended stay in a nursing home impoverishes even those who lived fairly comfortably prior to illness or injury. The cost of an average nursing home is $3333 per month. For the nonpoor elderly, the need for nursing home care often spells the end of financial as well as physical independence.

A person is not eligible to receive assistance from Medicaid unless their assets have been almost completely depleted. The extent to which assets must be "spent down" varies from state to state. All states permit an individual to keep a house, a car, a burial plot, burial funds, and a small amount of cash. However, states differ in terms of the maximum amount of cash savings and income that are allowed. In many states, cash savings are limited to two or three thousand dollars, and a personal monthly needs allowance of $30 or $40 is permitted. Once an individual depletes their assets to the point that they become eligible for Medicaid, they must still spend nearly all of their income—from Social Security benefits, pensions, interest, and dividends—on nursing home care before they can take advantage of the Medicaid program.

Existing financial planning tools provide insufficient information so as to enable one to select an appropriate course of action from the available health care funding alternatives. Instead, these tools merely generate a monthly or annual projection of overall cash flow during retirement. Individuals are then called upon to apply this information to a bewildering array of confusing alternatives. Due to the complexities of managing retirement health care expenses, it is easy for retirees and their families to become confused or overwhelmed at the available options As a result, many individuals do not follow a course of action that is appropriate or financially advantageous for their particular set of circumstances. The present situation is exacerbated in that unexpected health care expenses can lead to financial ruin.

OBJECTS AND SUMMARY OF THE INVENTION

In view of the prior art, it is an object of the invention to provide a financial planning tool that presents sufficient information so as to enable one to select an appropriate course of action from available health care funding alternatives.

It is a further object of the invention to apply various health care funding alternatives to a weekly, monthly, and/or annual projection of overall cash flow during retirement.

It is a still further object of the invention to provide a mechanism for managing retirement health care expenses that reduces or eliminates confusion on the part of retirees and their families.

It is yet a further object of the invention to provide a financial recommendation to a user recommending a course of action for financing possible future health care expenses that is appropriate and/or financially advantageous for a particular set of circumstances.

It is a still further object of the invention to help users avoid potential financial ruin by implementing a plan to meet possible unexpected health care expenses.

These and other objects of the invention are realized in the form of a computer-executable method for financial retirement planning that provides a comparative evaluation of a plurality of health care funding alternatives. The comparative evaluation enables individuals to select one or more funding alternatives appropriate to their particular set of circumstances. The method commences by calculating overall cash flow for an individual, a couple, and/or a family during retirement. Based upon this cash flow, an amount representing an affordable heath care insurance premium is determined. Next, a comparison of projected retirement finances is provided. This comparison provides (a) financial projections assuming that long-term health care will not be required, (b) financial projections if long-term health care is required, but the individual is not covered by insurance, and (c) financial projections if long-term health care is required, and the individual is covered by insurance. The financial projections include a level of attainable retirement spending per week, month, and/or year. Optionally, the projections include a low-cost estimate, an average cost estimate, and a high-cost estimate for the expenses of long-term health care and/or health care insurance.

BRIEF DESCRIPTION OF THE DRAWINGS

The above objects and advantages will become apparent to those skilled in the art upon reading the following detailed description of the preferred embodiments in conjunction with a review of the appended drawings, in which:

FIG. 9 is a line graph showing the impact of nursing home costs on retirement spending levels as a function of the length of time for which nursing home care is required;

FIG. 10 is a table showing annual achievable retirement spending levels with and without long-term health care insurance for three different levels of estimated health care or health care insurance expenses;

FIG. 11 is a table showing the cost of long term health care insurance as a function of age;

FIG. 12 is a table describing various features of a health coverage plan known as Medigap;

FIG. 13 is a table setting forth a cost comparison for long-term health care insurance coverage for a single or widowed client as a function of the purchase date of such coverage;

FIG. 14 is a table setting forth a cost comparison for long-term health care insurance coverage for a client and their spouse as a function of the purchase date of such coverage;

FIG. 15 is a table summarizing and explaining various salient features of typical long-term health care insurance policies;

FIG. 16 is a continuation of the table summarizing and explaining various salient features of typical long-term health care insurance policics;

FIG. 17 is a table comparing the features of various types of long-term health care programs such as Medicaid, long-term health care insurance, and Life Care Community.

FIG. 18 is a table comparing the features of various common short-term health care programs such as employer-provided retiree health care plans, COBRA, individual health insurance policies, Medicare, and Medigap;

FIG. 19 is a continuation of the table comparing the features of various common short-term health care programs such as employer-provided retiree health care plans, COBRA, individual health insurance policies, Medicare, and Medigap;

FIG. 20 is a table listing contact information for various institutions and agencies that are involved, either directly or indirectly, with long-term health care; and FIG. 21 is a table comparing the amount of money that an individual would leave to their heirs both with and without long-term health care insurance.

DETAILED DESCRIPTION OF THE PREFERRED EMBODIMENTS

Figure 1:
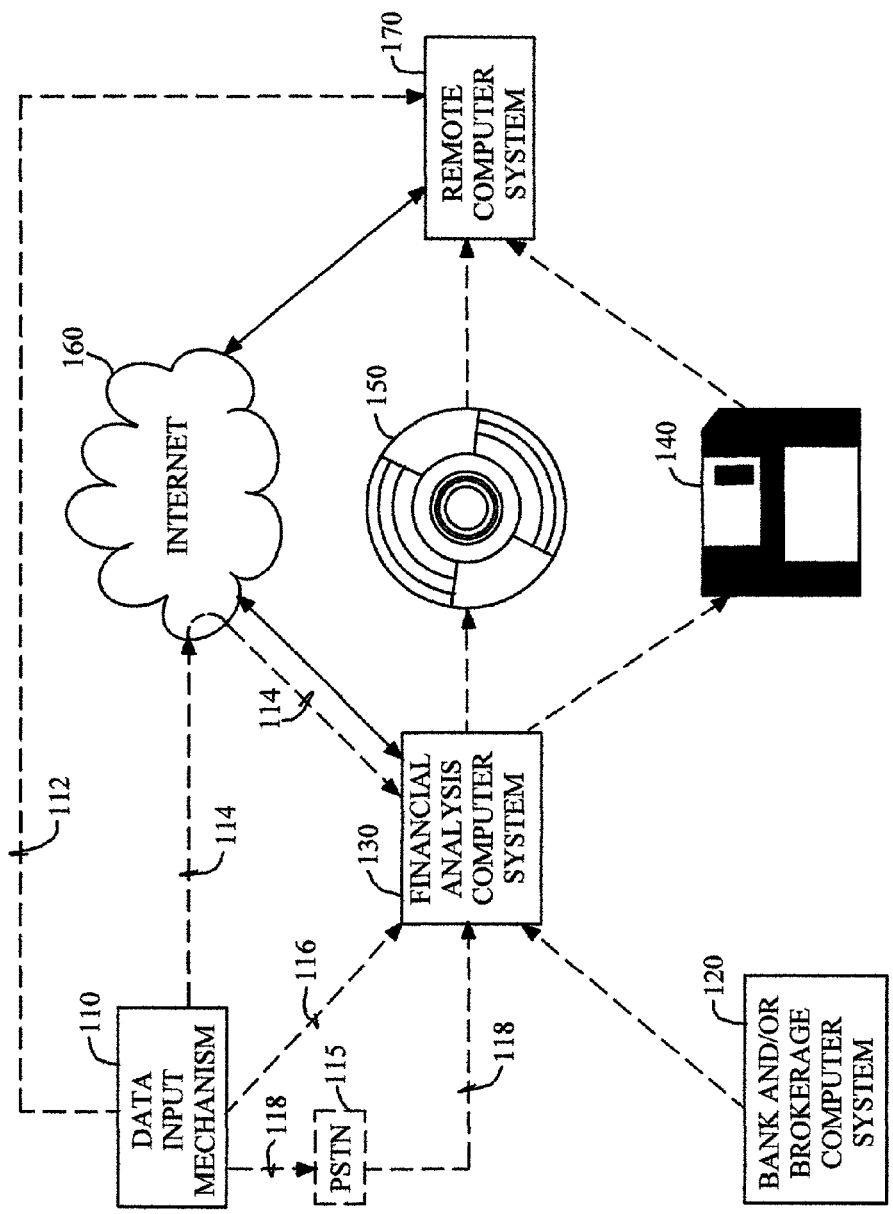
FIG. 1 is a hardware block diagram showing an illustrative system on which the techniques of the present invention are performed.

Refer now to FIG. 1, which is a hardware block diagram showing an illustrative system on which the techniques of the present invention are performed. Initially, financial data pertaining to one or more clients is received at data input mechanism 110. In practice, data input mechanism 110 may represent a computer keyboard, computer mouse, touch-sensitive display screen, modem, telephonic interactive voice response system, floppy disk drive, CD-ROM drive, or the like. In the case of an interactive voice response system or modem, data input mechanism 110 conveys received data through PSTN 115 to a financial analysis computer system 130 over communications path 118. Pursuant to other implementations, data input mechanism 110 is coupled to financial analysis computer system 130 via the Internet 160 over communications path 114, and/or data input mechanism 110 is coupled directly to financial analysis computer system 130 over communications path 116. Or, data input mechanism 110 may be coupled to remote computer system 170 which could represent the client's personal computer or a computer system used by the client's agent or representative.

Financial data received at data input mechanism 110 includes information related to any of the client's age, current income, expected retirement date, financial assets, bank accounts, Certificates of Deposit, Stock holdings, brokerage accounts, pension plans, 401K plans, retirement plans, any prior military service, and the like. Optionally, similar information may be imputed regarding the client's spouse, and/or some or all of the data could be entered in the form of one or more spreadsheets. Although relevant financial data concerning a client could be received at data input mechanism 110, some, none, or all of this data could be transmitted from a bank and/or brokerage computer system 120 to the financial analysis computer system 130. After the financial data are received at data input mechanism 110, and/or transmitted from bank and/or brokerage computer system 120, the data are associated with a client identifier that uniquely specifies a given client. The data and the client identifier associated therewith are stored in a computer-readable medium accessible from financial analysis computer system 130.

Financial information pertaining to a given client, and/or the client's spouse, is stored by financial analysis computer system 130 as a user profile. The computer-readable medium is used to store a plurality of user profiles corresponding to various clients. Specified user profiles can then be retrieved by financial analysis computer system 130 for subsequent analysis and display. Data input mechanism 110 may optionally include a provision by which the client (and/or the client's agent) is allowed to change and/or to update some of the stored data in this profile, such as current income. In this manner, future financial events may be considered and displayed, so that each set of financial information is tailored and pre-programmed specifically for a given user. Such a provision will reduce erroneous calculation results based on inadvertently entered, outdated, or corrupted data. Any changes, modifications, or updates to the user profile are then stored by financial analysis computer system 130 in the aforementioned computer-readable medium.

After financial data pertaining to a given user profile have been entered and stored, a sequence of calculations related to retirement health care expenses may be performed for the client corresponding to this user profile. The calculations can be initiated on demand by the client, the client's spouse, or an agent for the client. To this end, a request for a financial analysis of retirement health care expenses on behalf of a given client may be entered into data input mechanism 110, or directly into financial analysis computer system 130. According to one preferred embodiment of the invention, the aforementioned sequence of calculations is performed at financial analysis computer system 130. However, according to an alternate embodiment of the invention, the calculations are performed at remote computer system 170. In order to provide for execution of these calculations at remote computer system 170, the calculations are incorporated into one or more computer programs. These programs may be stored on a computer-readable medium such as a CD-ROM 150 or floppy disk 140, and then conveyed to remote computer system 170 for execution. Or, these programs could be offered over the Internet 160 in a downloadable format suitable for installation and execution at remote computer system 170.

Figure 2:
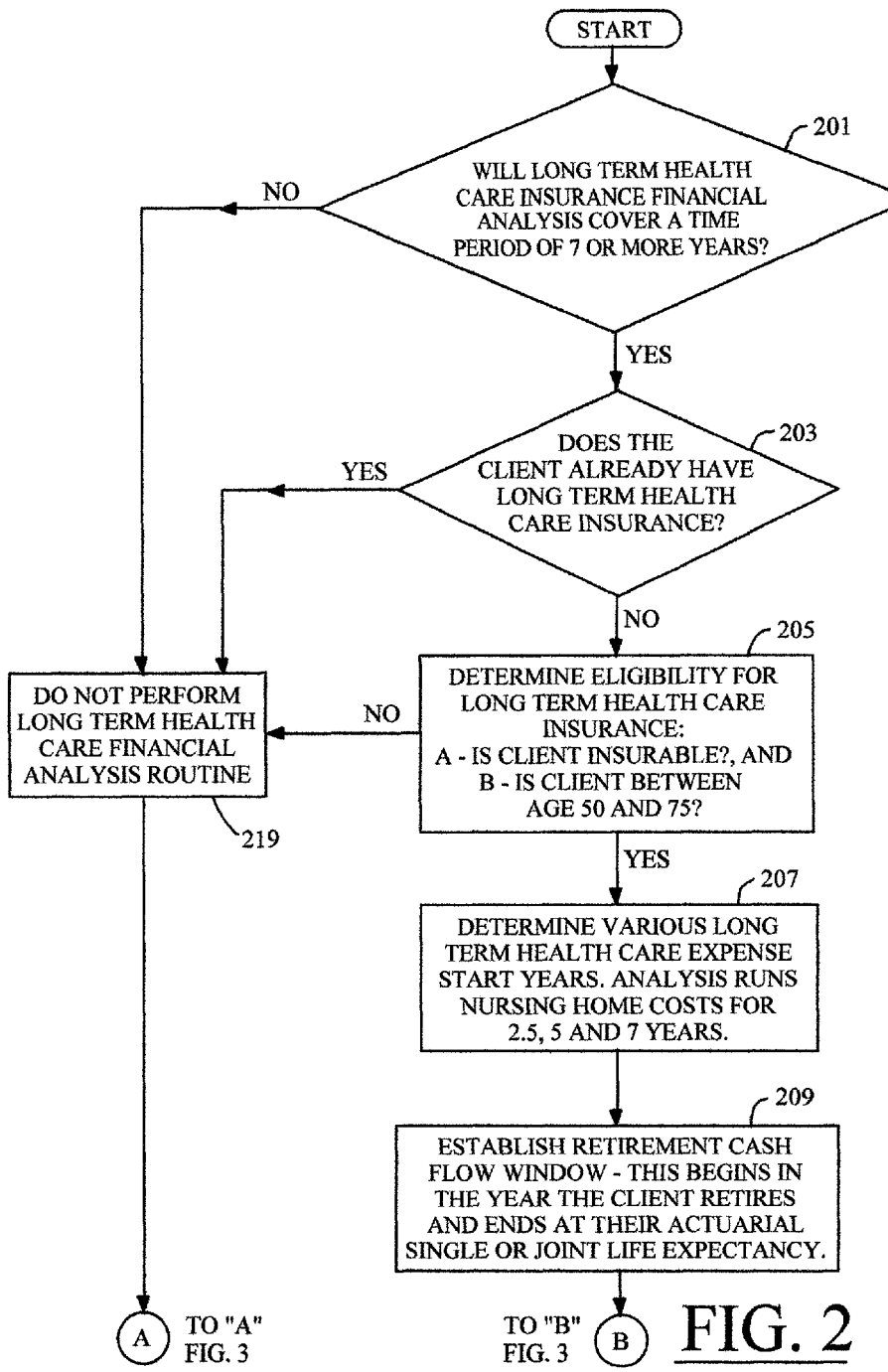
FIG. 2 is a flowchart setting forth an operational sequence for performing a retirement cash flow analysis of financial information according to a preferred embodiment of the present invention.

Refer now to FIG. 2, which is a flowchart setting forth an operational sequence for performing a retirement cash flow analysis of financial information according to a preferred embodiment of the present invention. The operational sequence commences at block 201 where a test is performed to ascertain whether or not the long-term health care insurance financial analysis will cover a time period of seven years or more. Of course, this time period may vary somewhat, depending upon the specifics of a given system application. Accordingly, the time period could be reduced to specify, for example, four years, or increased to specify eleven years, if desired. The negative branch from block 201 leads to block 219, signifying that the long-term health care financial analysis calculations will not be performed due to the analysis period being too short. The affirmative branch from block 201 leads to block 203 where a test is performed to ascertain whether or not the client already has long-term health care insurance. If so, then we do not wish to conduct a financial analysis and, accordingly, program control transfers to block 219 (discussed immediately above).

If the client does not already have long-term health care insurance, the program advances to block 205 where a test is performed to determine whether or not the client is eligible for long-term health care insurance. In order to be eligible, the client must satisfy both of the following conditions. First, the client must be insurable, and, second, the client must be between the ages of 50 and 75. Different insurers may have different criteria governing insurability. Accordingly, parameters in the client's user profile that are relevant to a given insurance company's determination of insurability must be retrieved from the user profile. These parameters are compared with insurance industry standards to determine whether or not the client is eligible for coverage. Optionally, these parameters are compared with the standards of the insurance company under consideration. If the client is not eligible for long-term health care insurance, program control advances to block 219, described above.

If the client is eligible for long-term health care insurance, the program progresses to block 207. A plurality of long-term health care starting years are determined for purposes of providing the client with a comparative evaluation of various alternative future scenarios. These starting years are calculated by considering the predicted length of nursing home stay that might be required, by considering the client's projected actuarial life expectancy, and by assuming that the nursing home stay will be required during the final years of this actuarial life expectancy. For example, a financial analysis may be commenced on the assumption that a nursing home stay might be required for a time period of 2.5 years, 5 years, or 7 years. Since clients are generally not able to predict with any degree of certainty when, or even if, they will require long-term health care, the use of a range of values is intended to provide clients with a spectrum of plausible alternatives that may be useful for purposes of financial planning. Accordingly, the time periods of 2.5, 5, and 7 years (during which long-term health care is required) can be adjusted upwards or downwards to meet the needs of specific system applications and/or clients. By way of example, one could perform these calculations assuming that the client will require long-term health care for a time period of 2, 4, or 6 years. Or, one could perform a multitude of calculations based upon nursing home stays of 1 year, 2 years, 3 years . . . and so on. These examples are given for illustrative purposes only, and are not intended to be limiting in any way.

After various long-term health care starting years are determined at block 207, the program advances to block 209 where a retirement cash flow window is calculated. This window commences on the client's retirement date and ends at the client's single or joint life expectancy. (Joint life expectancy considers the expectancy of the client as well as the client's spouse). Life expectancy information is obtainable from any of a number of generally available actuarial tables. Once the time duration of a client's retirement cash flow window has been calculated, the next step (block 211) is to determine the client's achievable retirement "lifestyle". As used herein, the term "lifestyle" refers to an annual spending level that the client is able to achieve throughout the cash flow window, while, at the same time, having little or no money left over at the end of this window. However, if the client wishes to have money left over at the end of this retirement window, the client may optionally specify a desired target retirement lifestyle figure, and/or a desired inheritance amount. These options are described in greater detail hereinafter with reference to FIG. 18. The achievable lifestyle is calculated for all combinations of high-cost, average-cost, and low-cost nursing homes, combined with each of the aforementioned time periods (for example, 2.5, 5, and 7 years). The achievable lifestyle is also calculated for all combinations of high-cost, average-cost, and low-cost health care insurance premiums.

Next, the program advances to block 213 where a test is performed to ascertain whether or not the client is able to afford to pay for the highest-cost nursing home for the longest duration of time (with reference to the above combinations) on an out-of-pocket basis. If not, the program advances to block 215 where financial analysis results are determined and formatted for display. The display formatting is implemented so as to indicate a comparison of an achievable retirement lifestyle if nursing home costs are paid out-of-pocket versus an achievable retirement lifestyle if nursing home costs are paid through a long-term health care insurance policy. This analysis considers the effect of insurance premiums on the latter alternative in determining the achievable retirement lifestyle. The formatted display information is then forwarded to Internet 160, remote computer system 170, and/or to a display terminal coupled to financial analysis computer system 130. The formatted display information is used to provide a visual display on a display screen and/or to generate a hard-copy report on a printer. The program then exits. Illustrative printouts and/or displays of the formatted information are set forth in FIGS. 4-18, to be described hereinafter.

The affirmative branch from block 213 leads to block 217 where financial analysis results are determined and formatted for display. The display formatting is implemented so as to implement a comparison of the amount of assets remaining at the end of retirement if nursing home costs are paid as out-of-pocket expenses, versus the amount of assets remaining at the end of retirement if nursing home costs are paid through a long-term health care insurance policy. This analysis considers the effect of insurance premiums on the latter alternative in determining the achievable retirement lifestyle. The formatted display information is then forwarded to Internet 160, remote computer system 170, and/or to a display terminal coupled to financial analysis computer system 130. The formatted display information is used to provide a visual display on a display screen and/or to generate a hard copy report on a printer. The program then exits. Illustrative displays of the formatted information are set forth in FIGS. 4-18, to be described hereinafter.

Figure 3:
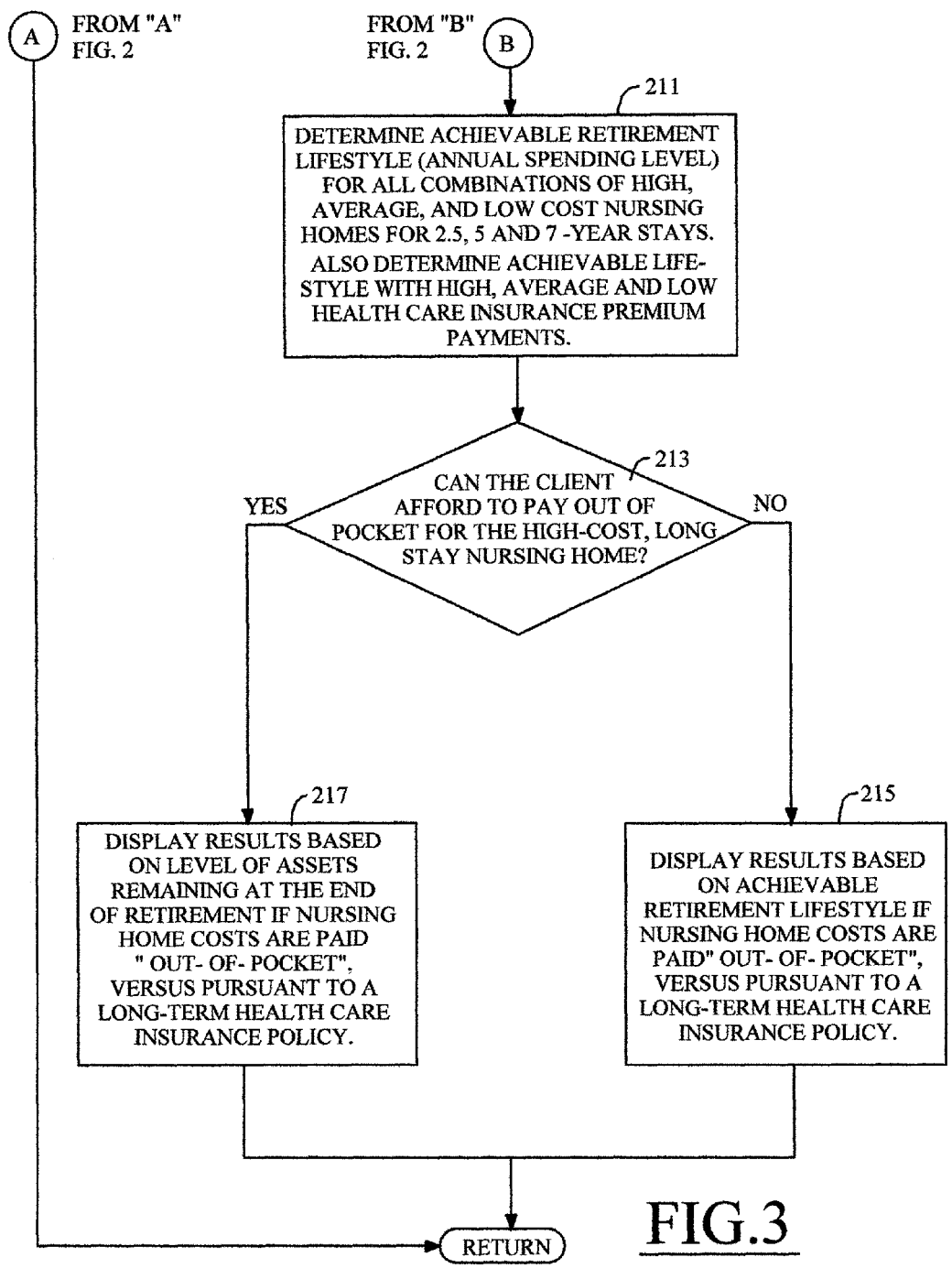
FIG. 3 is a flowchart representing a continuation of the operational sequence for performing a retirement cash flow analysis of financial information according to a preferred embodiment of the present invention.

FIG. 3 is a flowchart setting forth an illustrative operational sequence for determining an achievable retirement cash flow. The operational sequence of FIG. 3 may be used to implement block 211 of FIG. 2, described above. Note that achievable retirement cash flow is also referred to herein as an achievable retirement lifestyle. Returning now to FIG. 3, the program commences at block 301 where each of respective ending asset balances of previous years are rolled over to corresponding opening asset balances for the current year. Next, investment returns are calculated or simulated (block 303), and retirement plan contributions are determined (block 305). Retirement assets growth is determined (block 307), and the effects of any mandatory distributions are considered (block 309). The current year's tax is calculated, and the effects of any tax deficit or surplus are considered (block 311). After-tax income is calculated (block 315), and the effects of nursing home costs and long-term health care insurance premiums are also factored into the present analysis. The overall surplus or deficit is determined (block 317), and the results are then used in the analysis of block 211 (FIG. 2).

Figure 4:
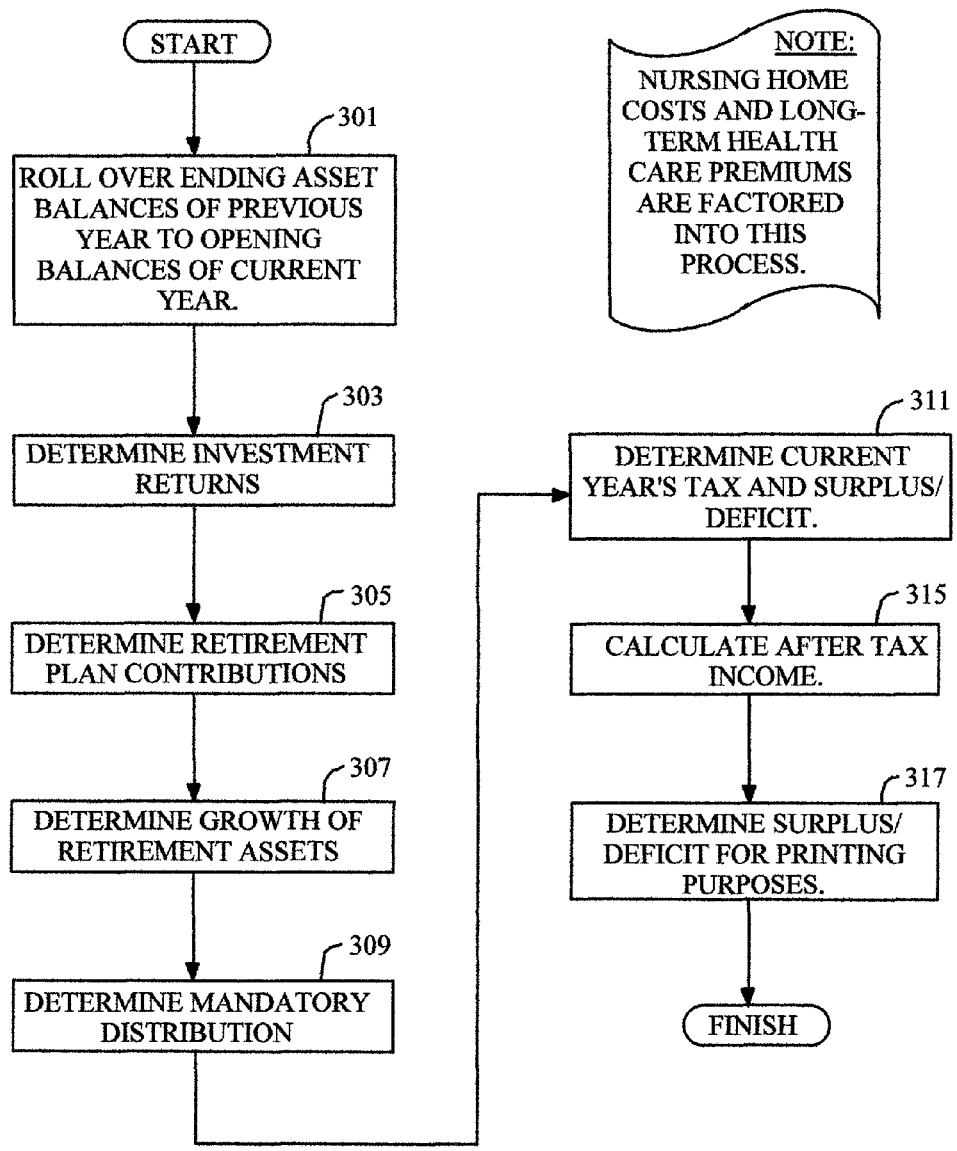
FIG. 4 is a flowchart setting forth an operational sequence for performing a long-term health care financing analysis according to a preferred embodiment of the present invention.

As stated above, illustrative displays of the formatted information generated pursuant to the procedures of FIGS. 2 and 3 are set forth in FIGS. 4-18. The bar graph of FIG. 4 depicts the annual spending level which an illustrative client would be able to achieve throughout retirement under three different sets of circumstances. Pursuant to a first set of circumstances, the client does not take steps to plan for long-term health care, but long-term health care is not required during retirement. If this scenario were to unfold, our client would be able to spend approximately $51,000 per year. This level of achievable spending is illustrated as bar 401, labelled "No Health Care Costs". The second set of circumstances is a scenario wherein the client plans for long-term care by purchasing an insurance policy that provides protection from nursing home costs. In this case, the premiums represent an additional expense, signifying that the client would have to reduce their spending level to $48,000 annually. This is illustrated as bar 403, labelled "Nursing Home Costs Paid By LTC Insurance". Finally, the third set of circumstances entails the client putting aside a sum of money that will be sufficient to cover future nursing home costs. Under this alternative, the client reduces their annual spending level, starting in the first year of retirement, to $34,500. This reduced spending level allows the client to set aside sufficient assets to cover a prolonged nursing home stay (seven years at $47,000 per year). This is illustrated as bar 405, labelled "Nursing Home Costs Paid Out-Of-Pocket".

Figure 5:
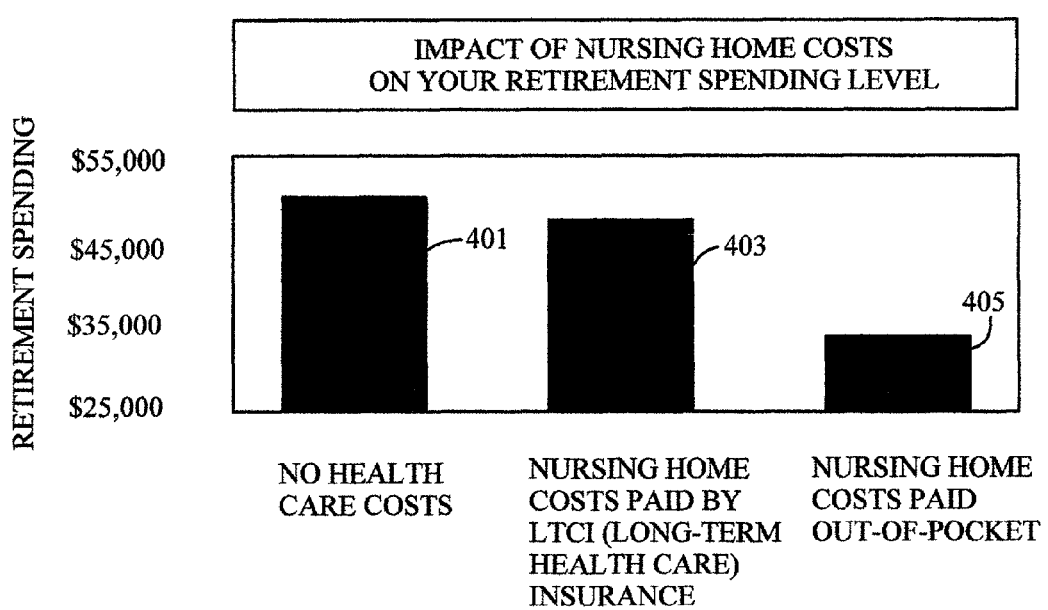
FIG. 5 is a bar graph that depicts the annual spending level which an illustrative client would be able to achieve throughout retirement under three different sets of circumstances.

FIG. 5 is an expense report setting forth the annual cost of long-term health care insurance premiums for an illustrative client as well as this client's spouse. Three different types of health care insurance policies are considered: a low-cost alternative, an average-cost alternative, and a high-cost alternative.

Figures 6, 7:
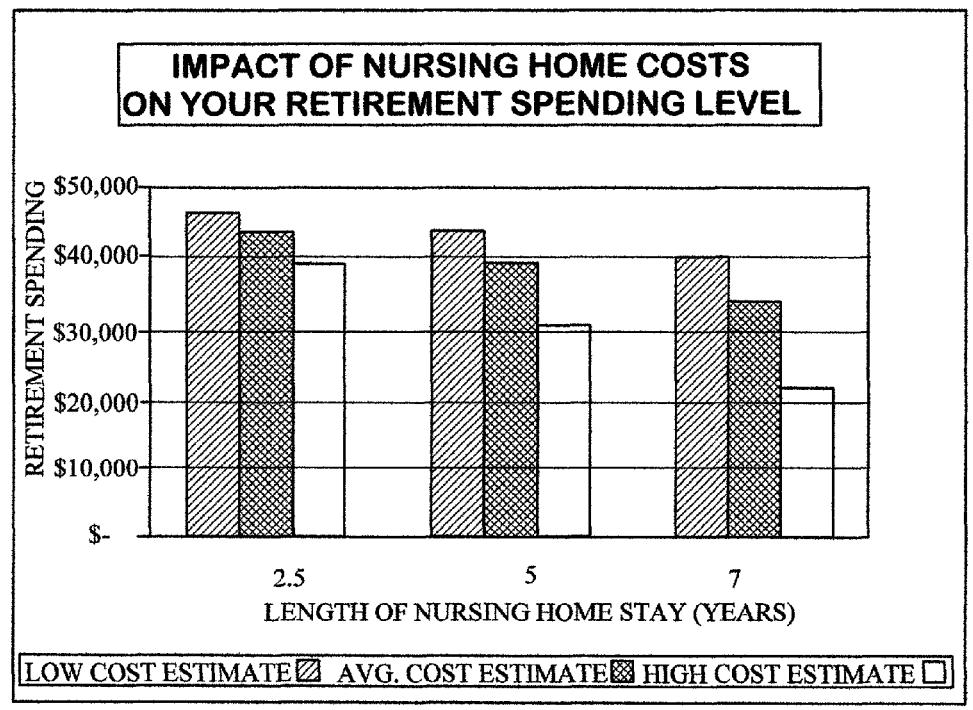
FIG. 6 is an expense report setting forth the annual cost of long-term health care insurance premiums for an illustrative client generated using the methods set forth in FIGS. 2 and 3.
FIG. 7 is a bar graph showing the potential impact of long-term health care expenses on an achievable retirement spending level for three different client scenarios.

FIG. 6 is a bar graph showing the potential impact of long-term health care expenses on an achievable retirement spending level for three different client scenarios and for three different nursing home cost estimates. The first client scenario assumes that a nursing home stay of 2.5 years will be required, whereas the second scenario considers a nursing home stay of 5 years, and the third scenario considers a nursing home stay of 7 years. For each of these nursing home length-of-stay durations, the costs of an inexpensive, average, and expensive nursing home is considered. The impact of these costs on annual retirement spending is graphically represented by the heights of the corresponding bars in FIG. 6.

FIG. 7 is a bar graph showing the achievable retirement spending level, both with and without long-term health care insurance, if a two-and-a-half year nursing home stay is required in the future. The analysis illustrates the effect of long-term health care insurance as an alternative to the client funding their long-term care needs out of pocket. The client's reduced retirement spending level is calculated for two scenarios:

Pursuant to a first scenario, costs associated with a 2½ year nursing home stay are paid for on an out-of-pocket basis by the client.

The resulting achievable lifestyle represents the reduced spending level that would be required in order to have sufficient assets available at the time that the client enters the nursing home.

Pursuant to a second scenario, costs associated with a 2½ year nursing home stay are paid for by a long-term health care insurance policy, for which the client pays annual premiums starting today and continuing throughout retirement.

The following assumptions have been made in developing the analysis graphically depicted in FIG. 7. First, it is assumed that either the client or the client's spouse would experience a need for nursing home care in the last three years of retirement. Second, nursing home costs used in this analysis are inflated annually at the current national average rate of 5.3%. This signifies that if a client, "Jim", was to enter a nursing home in 2020 (when Jim is age 83) the present (year 2001) $47,000 cost of a nursing home will have inflated to $139,000. Long-term health care insurance premiums have been estimated, for illustrative purposes, to be $4,600 per year, which includes:

$2,350 per year for Jim, based on his current age of 64.

$2,250 per year for Jane, who is Jim's spouse, based on her current age of 62.

These costs are added to the client's annual spending throughout retirement.

The bar graph of FIG. 7 shows that, across the full range of nursing home costs (low, average, high), the client's annual spending level would be higher if the client purchases a long teen care insurance policy versus paying for nursing home costs on an out-of-pocket basis. This means that self-funding long term health care needs would place a greater strain on the client's retirement spending than the premiums associated with long term health care insurance. However, the client's overall cash flow and spending needs could change significantly over time, and should be reevaluated periodically, and also at the time that the client needs to enter a nursing home.

From a practical standpoint, the bar graph of FIG. 7 may be used by a client to determine whether or not it is best for them to pay for long-term health care costs on an out-of-pocket basis. If a client chooses to pay for long-term care costs out-of-pocket, then this requires a reduced spending level throughout retirement. However, if the client does no require long-term care services, then the client will have an increased level of assets remaining to pass to their heirs. For example, based on the long-term health care analysis set forth in FIG. 7, if the client were to reduce their annual spending level from $50,000 to $44,5000 (the reduced spending level that is required if the client wishes to fund a 2½ year nursing home stay out-of-pocket based upon an average cost estimate), then the client would have an additional $400,000 in assets available for their heirs if they did not require nursing home care.

Figure 8:
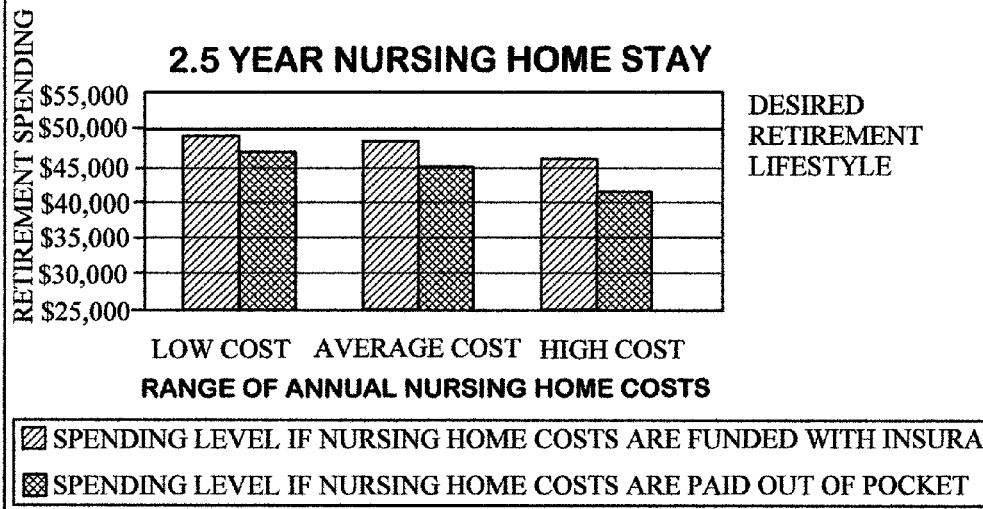
FIG. 8 is a bar graph showing the achievable retirement spending level, both with and without long-term health care insurance, if a two-and-a-half year nursing home stay is required in the future.

Refer now to FIGS. 8 and 9. FIG. 8 is a line graph showing the impact of nursing home costs on retirement spending levels as a function of the length of time for which nursing home care is required. FIG. 9 is a table showing annual achievable retirement spending levels with and without long-term health care insurance for three different levels of estimated health care or health care insurance expenses. An additional factor which most clients should consider is that, although the average length of a nursing home stay is two and a half years, a stay could vary in length. The graph of FIG. 8 presents a comparison of the client's reduced annual spending levels over varying lengths of stay in a nursing home if the client was to cover the expenses out-of-pocket. The table of FIG. 9 illustrates that, with long-term care insurance, the client's annual spending level varies only with the cost of insurance, and not with the length of the stay.

FIG. 10 is a table showing the cost of long term health care insurance as a function of age. The table sets forth a comparison of yearly premium costs for different ages at which a long-term care policy is initially purchased. Premiums increase as the client's age at the initial purchase of the policy increases.

The table of FIG. 11 sets forth various features of a health care coverage plan known as Medigap.

FIG. 12 is a table setting forth a cost comparison for long-term health care insurance coverage for a single or widowed client as a function of the purchase date of such coverage. Costs increase dramatically as the purchase date is advanced further and further into the future.

FIG. 13 is a table setting forth a cost comparison for long-term health care insurance coverage for a client and their spouse as a function of the purchase date of such coverage. As in the case of FIG. 12, costs increase dramatically as one procrastinates.

FIG. 14 is a table summarizing and explaining various salient features of typical long-term health care insurance policies. These policies typically have limits on the per-diem amount of money that an insured client will receive on a daily, weekly, monthly, or annual basis. Also, many of these policies do not provide instantaneous coverage as soon as the client is admitted to a nursing home. Rather, the amount of time that must elapse between the client first requiring long-term heath care and the client receiving policy benefits can vary from a minimum of zero to a maximum of 100 days. As a general matter, long-term health care policies may or may not provide coverage until the client is deceased. Coverage is typically offered for a fixed period of time, such as five years. Premiums increase as the duration of coverage increases.

FIG. 15 is a table comparing the features of various types of long-term health care programs such as Medicaid, long-term health care insurance, and Life Care Community. The table is designed to help the client consolidate various elements of health care coverage across a plurality of available benefit programs, so as to help the client offset their exposure to nursing home and other long-term health care costs. Medicaid and long-term health care insurance have already been described above. Briefly, a life care community provides for a client's housing and health care needs during retirement. A life care community is becoming a popular housing choice for many retirees. Facilities vary from single homes to apartments. Fees typically include a one-time charge plus monthly expenses. In addition to housing, retirees may receive light housekeeping, meal preparation, social and athletic opportunities and other perks. Clients typically receive various health care benefits, including guaranteed space in the facilities. In some instances, all or a portion of these costs have been pre-paid through up-front and monthly fees. Other medical services are often provided. These can range from blood pressure screening and flu shots to significant doctor and outpatient care. Once again, the costs may have been pre-paid through up-front and monthly fees.

FIG. 16 is a table comparing the features of various common short-term health care programs such as employer-provided retiree health care plans, COBRA, individual health insurance policies, Medicare, and Medigap. The table is designed to help the client consolidate the elements of coverage across a plurality of available benefit programs, so as to help the client offset their exposure to hospital and doctor costs.

FIG. 17 is a table listing contact information for various institutions and agencies that are involved, either directly or indirectly, with long-term health care.

FIG. 18 is a table comparing the amount of money that an individual would leave to their heirs both with and without long-term health care insurance.

APPENDIX "A"

Sample Report

Health Care
 In planning for retirement you should address your health care needs as they relate to:
  Hospital and Doctor Care
  Long-Term Care Hospital and Doctor Care
 Since you are retiring before age 65, you may no longer be covered by your employer's health plan and will most likely not yet qualify for Medicare.
 Consider your means for securing health care coverage during this time.

Long-Term Care
 Additionally, you should consider the impact a prolonged nursing home stay could have on your spending level throughout retirement. The chart of FIG. 4 depicts the annual spending level which you would be able to achieve throughout retirement (until 2022 with husband, Jim, at age 85 and wife, Jane, at age 84) under various circumstances including:

You do not take steps to plan for long-term care but do not require long-term care services during retirement. In this case you would be able to spend approximately $51,000 per year. This is illustrated as bar 401 (which, for example, is colored in green).

You plan for long-term care by purchasing insurance to provide protection from nursing home costs. In this case you would have to educe your spending level to $48,000 annually. This is illustrated as bar 403 (which, for example, is colored in blue).

You reduce your annual spending level starting in the first year of retirement of $34,500. This reduced spending level will allow you to set aside sufficient assets to cover a prolonged nursing home stay (seven years at $47,000 per year). This is illustrated as bar 405 (which, for example, is colored in red).

Estimated long-term care premiums used in this illustration are $4,600 per year.

National average annual nursing home costs are $47,000.

According to AARP research, about one-half of older people will spend some time in a nursing home—from as little as a few weeks to as much as five to seven years or more. If you do not take steps to prepare for long-term care, either by purchasing insurance or setting-aside additional assets, you many deplete your assets prematurely in the event of a prolonged illness. In the example on the previous page, if you did not take steps to plan for long-term care and were to suffer a prolonged nursing home stay, your assets would be depleted by 2017-when Jim is 80 and Jane is 79.

Variations in length of stay and nursing home costs will have a significant impact on the results of your long-term analysis. It is important to review these factors in light of your retirement lifestyle when making a decision regarding long-term care. These factors are addressed in further detail in the Analysis and Discussion section of your Financial Foundation.

Asset Protection

Explore your options for covering health care costs prior to age 65. During this time you may no longer be covered by an employer plan and will mostly likely not yet qualify for Medicare. Consider purchasing long-term care insurance to provide appropriate coverage in case of periods of prolonged illness. Consider reviewing your living trust and granting a durable power of attorney adequate protection in case of disability. Consider preparing medical directives (living will, medical power of attorney, etc.) to ensure that your intentions are carried out in the event of incapacity.

Health Care

Health Care Exposure

One of the most important considerations in planning for a comfortable retirement is ensuring that you can manage your health care expenses. There are two types of health care needs you should be prepared for:

(a) Hospital and doctor care (b) Long-term care

These concerns are faced by many retirees. According to AARP (American Association of Retired Persons), in 1998:

22% of retirees reported they had underestimated the money necessary to cover their medical expenses.

45% are not confident that they have saved enough to cover long-term care should it be needed.

To prepare for these potential expenses you should:

Identify health care benefits available to you,

Assess the limitations or exposures in your coverage, and

Weigh the choices of securing additional coverage (purchasing insurance) versus planning to cover expenses out of your own income and assets (self-funding). Each of these alternatives has potential risks:

Insurance—The risk associated with insurance is that you may sacrifice current income to pay premiums and never need the benefits.

Self-Funding—Health care expenses are potentially large and unpredictable in nature. As such, it is difficult to ensure that your assets will be sufficient in the event of a catastrophic illness or prolonged nursing home stay.

The following pages present your alternatives with regard to hospital and doctor care and long-term care. Analyses are included to help you quantify these alternatives to assist you in making the best decision for your personal situation.

Hospital and Doctor Care

The average cost per day of a hospital stay is $1,520. If you were to experience a catastrophic illness requiring a six-month stay in a hospital it would cost approximately $280,000. This only represents the cost for the hospital and does not include the cost of physicians, test, and medication. These costs represent a significant risk to your retirement lifestyle.

Because of your desired retirement age, there are two distinct exposures with respect to hospital and doctor care that you should prepare for:

(A) Hospital and doctor expenses that arise after retirement but before age 65 (post-retirement medical coverage). During this time individuals are typically no longer covered by an employer health plan and, unless disabled, will not yet qualify for Medicare.

(B) Hospital and doctor expenses after age 65 that may not be covered by Medicare (e.g., deductibles, co-payments, prescription drugs).

Post Retirement Medical Coverage

One of your primary concerns should be securing health care coverage between retirement and age 65. There are three potential alternatives for coverage during this time:

(A) Your employer may provide retiree health care coverage. Currently, only ⅓ of employers provide this type of coverage. You should consult with your employer's human resources department regarding this option. Please note, most employers retain the right to change their retiree health plan or even eliminate it.

(B) Continued coverage based on your employer's group plan for 18 months after retirement through a federal law known as COBRA.

(C) Personally owned, individual health insurance policies.

COBRA

Under a federal law known as COBRA (The Consolidated Omnibus Reconciliation Act) you and your spouse have the right to continue coverage under your employer's group health insurance plan for up to 18 months after your retirement. In addition, COBRA coverage could be available to you after retirement if your employer discontinues retiree health benefits. Below are some details about COBRA which will help you decide if this strategy is right for you.

COBRA coverage is not for everyone. The advantage of COBRA are that you pay at group rates which are typically cheaper than if you bought insurance on your own. In addition, you are guaranteed coverage and cannot be denied insurance based on pre-existing health problems. COBRA will be best for your situation if:

You aren't provided with retiree medical coverage from your former employer

You don't have a spouse's health plan under which you can be covered

You or your spouse are not yet eligible for Medicare (Medicare begins at age 65)

You have pre-existing health problems

You want to continue dental plans, vision plans and prescription drug plans your employer had but your new (post-retirement) insurance coverage does not have COBRA applies to the majority of employers. It does not apply, however, to employers with fewer than 20 employees and to many church and government employers.

As you approach retirement, you should receive notice from your employer regarding COBRA coverage. You may elect coverage pursuant to the terms and instructions provided with that notice. You usually have 60 days to make your election.

COBRA sets the minimum requirements that employers must meet. They can offer more continuation coverage if they choose. This is an issue you should discuss if you are negotiating an early retirement package.

The cost of coverage under COBRA is born solely by you. Costs will generally be higher than when you were employed since your employer was paying for part or all of coverage.

Personal Insurance

Personal insurance is an expensive alternative for meeting your health care needs. The cost of insurance rises significantly for older individuals. Additionally, your health condition will play a big part in determining your eligibility, as well as your annual premium. For married individuals in your age group, assuming good health, the combined annual cost of personal insurance would be roughly $4,000 to $7,000 per year.

Coverage after Age 65

Will Medicare be Sufficient?

Medicare is a federal health insurance program for people 65 or older (or permanently disabled) who are entitled to Social Security. Medicare coverage consists of two parts:

Part A (Hospital Insurance)

Part B (Medical Insurance)

[Add discussion Part C-Medicare Managed care for cohorts over age 65]

Both parts of Medicare have costs such as deductibles and coinsurance payments that you must pay either out-of-pocket or through other insurance coverage. The Medicare system is extremely useful but for many it will not be sufficient as the only form of heath care insurance in retirement.

Medicare Covers the Following:

In-Patient hospital care for up to 90 days in each "benefit period". In addition, a person has 60 lifetimes reserve days. A benefit period begins the day you are admitted to the hospital and ends 60 days after you are discharged. You can have more than one benefit period as long as you are out of the hospital for 60 days. Lifetime reserve days are "use them and lose them" nonrenewable days.

One hundred days of skilled nursing facility care. This care is for patients recovering from a hospital stay who need skilled medical services.

Doctor bills up to the reasonable and customary charge for services.

Emergency room and ambulance transportation

Home health care benefits

Hospice care benefits. A hospice is a facility for the terminally ill.

Outpatient hospital services

Medicare does not Cover:

Deductibles and coinsurance payments

Nursing home care

Elective surgery or experimental procedures

Care received outside of the U.S.

Dental care and dentures

Most routine checkups and tests

Most immunization shots

Most prescription drugs

Routine foot care

Eyeglasses, hearing aids

Retirees routinely require many of the products and services not covered by Medicare. As such, 78% of people age 65 and over feel it is necessary to supplement Medicare coverage. A popular vehicle for this supplemental coverage is Medigap Insurance.

Medigap Insurance

Medigap insurance is private insurance designed to supplement Medicare and provide protection for the "gaps" in the Medicare program. In other words, it eliminates the risk of unpredictable and uncontrollable bills by converting them into an affordable series of insurance payment. Medigap insurance is available through some employers as well as through private insurance contracts that you are eligible to buy automatically when you start Medicare, regardless of your health history.

Medigap insurance consists of ten standardized policies that cover incrementally greater amounts of benefits. The most comprehensive policies provide prescription drug coverage, which is excluded from the basic Medicare program. As you get closer to age 65, you will want to review the relative costs and benefits of these policies when purchasing Medigap insurance.

Summary Table

The table of FIG. 16 summarizes the health care sources discussed above. The table is designed to consolidate the elements of coverage across the various benefit programs available to help you offset your exposure to hospital and doctor costs.

Long-Term Care Services

Long-term care involves a wide variety of services for people with a prolonged physical illness, disability or mental incapacity. The national average cost of long-term care (extended care either at home or in a nursing home) is $47,000 per year. The average length of stay is 2½ years. If you were forced to pay these expenses out of pocket your annual retirement spending level could be significantly reduced.

Nursing home annual costs could vary depending on geographic location and the options or amenities offered at the facility from $30,000 to $80,000. To cover these costs would require combined annual long-term care premiums ranging from $3,100 to $8,600. Your long-term care analysis show the impact on your retirement lifestyle for high and low cost estimates, as well as the national average.

Who Pays for Long-Term Care?

Medicare—Medicare does not cover the cost of long-term care. Medicare may cover the cost of some care in a skilled nursing facility or at home, but only in limited situations and only for 100 days.

Personally Funded—Approximately one-third of all nursing home expenses are paid out of the assets of individuals requiring long-term care and their families.

Medicaid—About half of all nursing home expenses are paid by a Medicaid program. To qualify for Medicaid nursing home coverage, you must decrease your investment assets to the point of impoverishment based on the rules of your state.

Long-Term Care Insurance—Long-term care insurance is a growing alternative that individuals are selecting to cover potential long-term care costs.

Medicaid

As noted above, Medicaid pays for the largest portion of long-term care costs in this country. However, to qualify for Medicaid coverage you must decrease your assets to the point of impoverishment base on the rules for your state. In most states, your total assets (excluding the house you, your spouse or your child live in and some other assets like cars, term insurance, personal belonging, the corpus of an income-only trust, etc.) must be worth between $1,000 to $4,000. In addition, monthly income must not exceed your state's guideline. Furthermore, you must contribute the majority of your own income towards your care. The at home spouse is allowed to keep a minimal amount of income and assets. If you gift within 36 months of your application for benefits, those gifts may be counted in determining whether you met the asset level limits. If a trust is involved with the gift, the look-back period can be as long as 60 months. If an individual applies for Medicaid during the time they would be deemed ineligible due to a gift transfer, the individual and or his/her advisors may be prosecuted for fraud.

Long-Term Care Insurance

Long-Term Care Analysis

The analysis set forth in the chart of FIG. 7 illustrates the effect of long-term care insurance as an alternative to funding your long-term care needs out of pocket. Your reduced retirement spending level is calculated for two scenarios:

Costs associated with a 2½ year nursing home stay are paid for out of pocket by you. The resulting achievable lifestyle represents the reduced spending level that would be required in order to have sufficient assets available at the time you enter the nursing home.

Costs associated with a 2½ year nursing home stay are paid for by a long-term care insurance policy, for which you pay annual premiums starting today and continuing throughout retirement.

Assumptions

The following assumptions have been made in developing this analysis:

One of you would experience a need for nursing home care in the last three years of retirement. Nursing home cost used in your analysis are inflated annually at the current national average rate of 5.3%. This means that if you were to enter a nursing home in 2020 (when Jim is age 83) the $47,000 nursing home cost will have inflated to $139,000.

Long-term care insurance premiums have been estimated for illustration purposes at $4,600 per year, which includes:

$2,350 per year for Jim based on his current age of 62.

$2,250 per year for Jane based on her current age of 61

These costs are added to your annual spending throughout retirement.

Across the full range of nursing home costs (low, average, high) your annual spending level would be higher if you purchase a long term care insurance policy versus paying for nursing home costs out of pocket. This means that self funding your long term care needs would place a greater strain on your retirement spending than the premiums associated with long term care insurance.

Keep in mind, however, that your overall cash flow and spending needs could change significantly and should be reevaluated at the time you were to enter a nursing home.

Self-Funding Consideration

While choosing a pay for long-term care costs out-of-pocket would require a reduced spending level throughout retirement, if you do no require long-term care services you will have an increased level of assets remaining to pass to your heirs as a result.

For example, based on your long-term care analysis, if you were to reduce your annual spending level from $50,000 to $44,5000 (your reduced spending level if you wish to fund a 2½ year nursing home stay out-of-pocket-average cost estimate) you would have an additional $400,000 in assets available for your heirs if you did not require nursing home are.

Longer Nursing Home Stay

An additional factor to consider is that although the average length of stay is two and a half years, a nursing home stay could vary in length. The table of FIG. 8 presents a comparison of your reduced annual spending levels over varying lengths of stay in a nursing home if you were to cover the expenses out-of-pocket. The table of FIG. 9 illustrates that, with long-term care insurance, your annual spending level varies only with the cost of insurance, and not with the length of the stay.

Selecting a Long-Term Care Insurance Policy

When selecting a long-term care policy, you must consider the following factors:

Your age;

health status and family medical history;

policy features; and potential tax considerations associated with long-term care insurance premiums.

Your age, health and the policy features that you choose will have an impact on the premium that you pay for your policy.

A "qualified policy" is one that is structured to reflect Internal Revenue Code requirements for receiving favorable tax treatment. You can still buy non-qualified policies that do not meet these requirements. The choice between qualified and non-qualified depends on which offers more of the benefits you want, and costs less after taxes.

Age

Premiums increase depending on your age at the initial purchase of the policy. The table of FIG. 10 is a comparison of yearly premium costs at different ages of a long-term care policy purchase:

Health

Insurance companies look at your health and health history before they will issue you a long-term policy. Certain health conditions can result in a premium increase of 30% to 75% over the standard risk class premium (e.g. diabetes, cardiovascular disease). Generally, though, it is not likely that you will be "rated-u" based on health conditions. You will either be eligible or not eligible based on your health.

Features Selected for Your Analysis

The policy illustrated in Your Long-term Care Analysis included the following features and benefits. These features are summarized in the table of FIG. 18:

Daily benefit amount for the following:
$80 per day to cover a $30,000 nursing home cost
$130 per day to cover a $47,000 nursing home cost
$220 per day to cover a $80,000 nursing home cost 100 day elimination period 5% compound increase for inflation 80% home health care benefit amount Standard risk class 10% marital discount No optional benefits The estimated premiums do not take into consideration your current health situations which could have an impact on your actual premium amounts.

Tax Considerations

Benefits received under a long-term care policy are generally not included as taxable income. Additionally, under new legislation (The Health Insurance Portability & Accountability Act of 1996 which became effective Jan. 1, 1997) it is possible that your long-term care policy premiums will count as an itemized medical expense on your tax return. Consult your tax advisor for further details.

Your Next Step

Potential long-term care costs should be an important consideration when evaluating your overall financial plan. Your financial objectives (e.g., a comfortable retirement or passing wealth to your heirs) should also be reviewed in light of the potential impact of long-term care. We recommend that you contact your advisors and Financial Consultant, Joe Smith, prior making any long-term care protection decisions.

Life Care Communities

As you plan for retirement, you may want to consider the features of a life care community for your housing and care needs during retirement. A life care community is a popular housing choice for many retirees. Facilities vary from single homes to apartments. Fees typically include a one-time charge plus monthly expenses. In addition to housing, retirees may get light housekeeping, meal preparation, social and athletic opportunities and other perks. Of importance to our discussion is that you will also typically get the following health care benefits.

Guaranteed space in the facilities" nursing home or skilled nursing facility—in some instances some or all of the costs have been pre-paid through the up front and monthly fees.

Other medical services—these can range from blood pressure screening and flu shots to significant doctor and outpatient care. Once again, the costs may have been pre-paid through the up front and monthly fees.

Summary Table

The table of FIG. 15 summarizes the long-term care sources discussed above. The table is designed to consolidate the elements of coverage across the various benefit programs available to help you offset your exposure to nursing home and other long-term care costs.

Legal Affairs

Who would Make Decisions for You if You were Mentally Incapacitated?

If you were to become mentally incapacitated, decisions regarding your health, well-being, disposition of assets, etc., would be made by a court-appointed guardian and/or conservator unless you take proper steps to prepare for this possibility. (Even a spouse must obtain court approval to assume control of property owned separately.) Two alternatives to consider are setting up a living trust or creating a durable power of attorney.

Living Trust

Establish and fund a living trust, appointing yourself as trustee to retain control of the assets in the trust.

Appoint a successor trustee to take control of the assets, and the income from those assets, if you should lose capacity to make legal decisions.

This gives you the opportunity to choose a person in whom you have confidence, such as your spouse or trusted advisor, to make the decisions that may be necessary for your well-being.

Durable Power of Attorney

Create a durable power of attorney, retained in your attorney's office, to be activated if you should become incapacitated. This gives immediate control of your assets, and the income from those assets, to a surrogate in whom you have confidence to make decisions on your behalf. We recommend that you discuss the mechanics and costs of these and other possible alternatives with your attorney and choose the one that you find most desirable.

Medical Directive

At the same time, we recommend that you consider establishing a medical directive. A medical directive tells your medical caregivers your wishes regarding medical treatment if you are unable to communicate. There are two types of medical directives:

Living Wills—these specify whether or not "heroic" measures should be used to prolong life in the event of a terminal illness.

Medical Power of Attorney—also known as a Durable Power of Attorney for Health Care.

This document can be used to:

Empower an individual to make decisions on your behalf at any time you are unable to make your own decisions (even if you are not terminally ill);

Specify whether or not "heroic" measures should be used.

Specify visitation rights;

Important Documents

Add brief discussion including the following items:

Who should you pick as trustee, power of attorney?

Where do you keep your documents?

Who knows about your directives, arrangements?

Where is the key?

Other Insurance

The remainder of this section reviews your need for adequate protection against financial losses due to:

property damage;

liability claims.

It is important to periodically review all of your current insurance policies to:

determine adequate protection;

take advantage of discounts that may be available for reduced probability of claim (e.g., alarm system).

Homeowner's Insurance

Inadequate coverage against loss of or damage to your home or personal property can expose you to unnecessary risk.

Review your coverage periodically.

Home

Insurance companies generally require you to insure at least 80% of your home's full replacement value. We recommend that your insurance policy cover the full "replacement cost" of your home. Most policies include basic coverage which specifies cash value or market value of the home. Replacement cost coverage may cover your risk more adequately especially if you have been in your home for a long time.

We claim:

1. A computer-executable method for financial retirement planning that provides a comparative evaluation of a plurality of health care funding alternatives, so as to enable an individual to select one or more funding alternatives appropriate to their particular set of circumstances; the method comprising the steps of:

(a) calculating, at a computer, an overall retirement cash flow for an individual, a couple, and/or a family representing funds available during retirement;

(b) determining an amount representing an affordable long-term health care insurance premium, based upon the retirement cash flow calculated in step (a); and (c) generating a comparison of projected retirement finances for display on at least one of a visual display and a hard-copy printout, wherein the step of generating a comparison further includes the steps of:

(a) determining one or more financial projections assuming that long-term health care will not be required;

(b) determining one or more financial projections if long-term health care is required, but the individual is not covered by insurance; and (c) determining one or more financial projections if long-term health care is required, and the individual is covered by insurance.

2. The method of claim 1 wherein the financial projections include a level of attainable retirement spending as a function of time.

3. The method of claim 2 wherein the financial projections include a level of attainable retirement spending per week, month, and/or year.

4. The method of claim 2 wherein the financial projections include at least two of a low-cost estimate, an average cost estimate, and a high-cost estimate for the expenses of long-term health care.

5. The method of claim 2 wherein the financial projections include at least two of a low-cost estimate, an average cost estimate, and a high-cost estimate for the expenses of a long-term health care insurance policy.

6. The method of claim 2 wherein the financial projections include at least two of a low-cost estimate, an average cost estimate, and a high-cost estimate for the expenses of a long-term health care insurance policy and the expenses of long-term health care.

7. A computer system for executing a financial retirement planning program that provides a comparative evaluation of a plurality of health care funding alternatives, so as to enable an individual to select one or more funding alternatives to their particular set of circumstances, the system including:

(a) a processing mechanism for:

(i) calculating an overall retirement cash flow for an individual, a couple, and/or a family representing funds available during retirement;

(ii) determining an amount representing an affordable long-term health care insurance premium, based upon the retirement cash flow calculated in (i);

(iii) determining one or more financial projections assuming that long-term health care will not be required;

(iv) determining one or more financial projections if long-term health care is required, but the individual is not covered by insurance; and (v) determining one or more financial projections if long-term health care is required, and the individual is covered by insurance; and (b) a display formatting mechanism for generating a formatted display indicative of a comparison of projected retirement finances for each of a plurality of long-term health care scenarios, wherein the formatted display is suitable for display on at least one of a visual display device and a hard-copy printout; the long-term health care scenarios including at least two of:

(i) the individual not obtaining long-term health care insurance, but subsequently not requiring any long-term health care;

(ii) the individual not obtaining long-term health care insurance, but subsequently requiring long-term health care and paying for such long-term health care on an out-of-pocket basis; and (iii) the individual obtaining long-term health care insurance.

8. The computer system of claim 7 wherein the financial projections include a level of attainable retirement spending as a function of time.

9. The computer system of claim 8 wherein the financial projections include a level of attainable retirement spending per week, month, and/or year.

10. The computer system of claim 8 wherein the financial projections include at least two of a low-cost estimate, an average cost estimate, and a high-cost estimate for the expenses of long-term health care.

11. The computer system of claim 8 wherein the financial projections include at least two of a low-cost estimate, an average cost estimate, and a high-cost estimate for the expenses of a long-term health care insurance policy.

12. The computer system of claim 8 wherein the financial projections include at least two of a low-cost estimate, an average cost estimate, and a high-cost estimate for the expenses of a long-term health care insurance policy and the expenses of long-term health care.

* * * * *